United States Patent [19]

Ginsberg et al.

[11] Patent Number: 4,820,505

[45] Date of Patent: Apr. 11, 1989

[54] DETECTION OF ACTIVATED PLATELETS WITH ANTIBODIES TO THROMBOSPONDIN

[75] Inventors: Mark H. Ginsberg; Edward F. Plow, both of San Diego, Calif.

[73] Assignee: Scripps Clinic and Research Foundation, La Jolla, Calif.

[21] Appl. No.: 720,032

[22] Filed: Apr. 4, 1985

[51] Int. Cl.$^4$ ............... A61K 49/00; G01N 33/53
[52] U.S. Cl. ....................... 424/9; 424/1.1; 424/4; 424/85.8; 435/7; 435/68; 435/172.2; 435/240.27; 435/243; 435/810; 435/948; 436/501; 436/503; 436/504; 436/547; 436/806; 530/387; 530/808; 530/809; 935/89; 935/93; 935/95; 935/106
[58] Field of Search ............... 424/1.1, 4, 9, 85; 436/501, 503, 504, 547, 548, 806; 435/68, 172.2, 243, 948, 810, 7, 240.27; 530/387, 808, 809; 935/89, 93, 95, 106

[56] References Cited

U.S. PATENT DOCUMENTS

3,789,116  1/1974  Kay ............................ 436/547
4,610,960  9/1986  Mosher .

OTHER PUBLICATIONS

Powers, et al. Neurology, vol. 32, (1982), pp. 938–943.
Kohler, et al. Nature, vol. 256, (1975), pp. 495–497.
American Type Culture Collection Catalogue of Cell Lines and Hybridomas, Sixth Edition, (1988), p. 323.
Aiken et al., *Blood*, 69:58–64 (1987).
Lawler et al., J. Biol. Chem. 253:8609 (1978).
Nieuwenhuis et al., Thrombosis and Haemostasis 50:100 (1983).
Hsu–Lin et al., Blood 62(Suppl. 1) (1983).
McEver et al., Blood 62(Suppl. 1) (1983).
Raugi et al., J. Cell. Biol. 95:351 (1982).
Mosher et al., J. Cell. Biol. 93:343 (1982).
Jaffe et al., Proc. Natl. Acad. Sci. USA 80:998 (1983).
Jaffe et al., Nature 295:246 (1982).
Nurden et al., Thrombosis and Haemostasis 50:132 (Abst.) 401 (1983).
Shulman et al., Nature 276:269 (1978).
Galfre et al., Nature 277:131 (1979).
Goding, "Production of Monoclonal Antibodies by Cell Fusion", in *Antibody as a Tool*, Marchalonis et al. Eds., John Wiley & Sons Ltd., 273–289 (1982).
Berman et al., J. Clin. Invest. 78:130 (1986).
Gartner et al., Thromb. Haemostas. (Stuttgart) 52:354 (1984).
Hsu–Lin et al., J. Biol. Chem. 259:9121 (1984).
Wolff et al., J. Biol. Chem. 261:6840 (1986).

*Primary Examiner*—Esther M. Kepplinger
*Assistant Examiner*—Stephen C. Wieder
*Attorney, Agent, or Firm*—Dressler, Goldsmith, Shore, Sutker & Milnamow, Ltd.

[57] ABSTRACT

A diagnostic site-specific imaging reagent in the form of a receptor and an indicating means selectively binds to a specific cell membrane-associated antigen of a blood platelet that is in a stimulated active state but does not substantially bind to a platelet that is in a non-stimulated resting state. In particular, prelabelled monoclonal antibodies and polyclonal antibodies are prepared that bind and image thrombospondin when it is cell membrane-associated on a thrombin-stimulated platelet, thereby providing means for detecting and discriminating between a stimulated active blood platelet and a non-stimulated resting blood platelet.

26 Claims, No Drawings

DETECTION OF ACTIVATED PLATELETS WITH ANTIBODIES TO THROMBOSPONDIN

TECHNICAL FIELD

The present invention relates to a diagnostic site-specific imaging reagent that binds to a specific mammalian cell membrane-associated antigen on the cell membrane of a stimulated activated platelet but that does not substantially bind to a non-stimulated resting platelet, a method of preparing the reagent and its use in a diagnostic system for detecting, indicating and localizing stimulated platelets. More particularly, the present invention relates to monoclonal and polyclonal receptors that bind to a specific cell surface-expressed intracellular blood protein component.

BACKGROUND

Mammalian blood contains small cells known as platelets. Human platelets are anucleate circulating particles with a diameter of about 2-4 micrometers. Platelets that circulate freely through blood vessels as free floating cells are known as "resting" platelets.

Intact, resting platelets are normally non-adhesive and exhibit limited interaction with intact endothelium or with other blood cells. However, these platelets are rapidly converted from free floating cells to an adhesive aggregate mass of intact platelets, known as "activated platelets", during the process of hemostasis or during the formation of thrombi.

When the wall of a blood vessel is damaged as from a blow or as a result of vascular event, a hemostatic response is rapidly elicited to prevent excessive blood loss. This response, as it has evolved in higher organisms, is triggered to efficiently seal and localize hemostasis by the concerted action of blood platelets and the coagulation system. In contrast, in vessels injured by chronic disaases; e.g., atherosclerosis, activated platelets may adhere to each other and to the vessel wall leading to thrombotic occlusion. Such events occur in heart attack and stroke with venous embolism. Blood platelets are transported to the site of the injury and aggregate to form a hemostatic plug. Fibrinogen then assists in forming a clot.

The involvement of blood platelets in primary hemostasis and thrombosis is initiated by surface contact interactions and is contingent upon the adhesive properties of the platelet cell. Three general phenomena comprise an adhesive event: (1) attachment of the platelet to the substratum, such as the subendothelial matrix; (2) spreading of the platelet which establishes additional contact sites with the substratum; and (3) recruitment of additional platelets to form aggregates. Platelet aggregation can be stimulated by exposure of the cell to adenosine-5'-diphosphate (ADP), ADP/fibrinogen, epinephrine, thrombin, serotonin, collagen and certain arachidonic acid metabolites.

The expression of adhesive properties in a resting human blood platelet therefore is initiated by an appropriate stimulus that regulates the adhesive response. The stimulation transforms blood platelets from a non-adhesive "resting" state to an adhesive "activated" state that supports adherence of the platelets to blood vessels and to one another to form thrombi. Thus, the alteration of the adhesive properties of these cells plays a crucial role in host defense mechanisms and in the pathogenesis of thromboembolic disease.

The terms "non-stimulated platelet" and "resting platelet" are used interchangeably herein to denote a normal free flowing blood platelet that has not been exposed to a physiological stimulus as previously described, and which is, therefore, in a "non-adhesive" or "intact" state. Conversely, the terms "stimulated platelet" and "activated platelet" are used interchangeably herein to denote a blood platelet that has been exposed to a physiological stimulus as described, and which is, therefore, in an "adhesive" state.

During hemostasis and thrombosis, resting blood platelets are known to change morphologically in shape and biochemically in cell surface membrane composition during aggregation and secretion. The platelets change in shape from disks to spheres with long pseudopods that aggregate with adjacent platelets. The activated platelets secrete their granule contents into the surrounding environment, accelerate plasma coagulation, bind developing fibrin strands and provide the impetus for clot retraction.

A study of platelet surface membrane changes following the stimulation of resting platelets with thrombin showed that major platelet surface membrane changes occur after secretion but not after reversible aggregation. See George et al., *J. Clin. Invest.*, 66, 1 (1980) which is incorporated herein by reference.

Another study of the action of thrombin on intact human blood platelets related to the presence of a new cell membrane-associated protein that was not fibrinogen. Baenziger et al., *Proc Natl Acad. Sci. (U.S.A.)*, 68, 240 (1971) which is also incorporated herein by reference. This new membrane protein has since been identified as "thrombospondin" and is sometimes also known as "thrombin-sensitive protein" or "glycoprotein G".

Thrombospondin is a filamentous macromolecule measuring about $7 \times 70$ nanometers (nm) that appears to be a major subcellular blood protein component [Lawler et al., *J. Biol. Chem.*, 23, 8609 (1978)]. Lawler et al. also reported that thrombospondin comprises three disulfide-linked chains of about 142,000 to about 190,000 daltons each which may or may not be identical. Thrombospondin contains approximately 4 percent by weight carbohydrate, with neutral sugars, amino sugars and sialic acid (N-acetylneuraminic acid) in a weight percent ratio of about 4:3:1.5, and contains no hexuronic acid.

From studies of patients with quantitative deficiencies of certain plasma proteins, platelet adhesivity is believed to be mediated or modulated by selected "adhesive proteins" in addition to the foregoing stimulus requirement.

Adhesive proteins are cofactor proteins that are expressed at the outer cell surface of an activated blood platelet These proteins are usually either completely absent from the outer cell surface of intact resting platelets or are present only in minimal quantities. Thus, cell membrane-associated adhesive proteins are believed to be primarily expressed as intracellular components, and in some instances as extracellular components.

Adhesive proteins that have been identified on the outer cell membrane surface of activated platelets include fibrinogen, fibronectin, von Willebrand factor (also known as Factor VIII) and thrombospondin. These four proteins share common characteristics in that they (1) are normally absent from the outer cell surface of resting platelets; (2) interact minimally with non-stimulated intact platelets; (3) are expressed at the cell surface following platelet stimulation and (4) have gross structural similarities. Proposed mechanisms for the expression of these four adhesive proteins at the outer cell membrane platelet surface are discussed in Ginsberg and Plow, *J. Supramolecular Structure and Cellular Biochem.*, 17, 91 (1981).

Although the primary sequence homologies between the proteins are not fully known, selected structural features of the four proteins are similar. All four adhesive proteins described above, are glycosylated macromolecules having an element of internal symmetry in their multimeric state. In particular, fibrinogen has a molecular weight of about 340,000 daltons and has a dimeric structure made up of a plurality of subunits having molecular weights of about 48,000, 56,000 and 65,000 daltons. Fibronectin has a molecular weight of about 450,000 daltons and circulates primarily as a dimer of two very similar, but not identical disulfide-linked subunits having a molecular weight of about 220,000 and 230,000 daltons, respectively. Higher multimers of fibronectin are known to occur in plasma and may predominate in the matrix. Thrombospondin exists as a trimer having a molecular weight of about 450,000 daltons with three disulfide-linked subunits of very similar sizes having a molecular weight of from about 142,000 to about 190,000 daltons. von Willebrand Factor is composed of 220,000 dalton subunits that multimerize to yield a molecular weight of about 1,000,000 to about 20,000,000 daltons.

Plasma and extracellular matrices are believed to constitute the primary exogenous sources of the above four adhesive proteins. With the exception of thrombospondin, plasma is the major potential source of the other three adhesive proteins. Saglio et al. have reported thrombospondin to be 3 to 5 orders of magnitude less abundant than fibronectin or fibrinogen at a concentration of 20–130 nanograms (ng)/milliliter (ml) in blood plasma [*Blood*, 59, 162 (1982)].

It is known that, upon exposure to thrombin, blood platelets mobilize certain submembranous cytoplasmic storage granules (alpha granules) that release their contents into the environment. Platelet storage granules contain a number of proteins that are normally absent from the cell surface of a resting blood platelet, but that are present as cell surface associated membrane proteins of thrombin-stimulated "activated" platelets. It is further believed that the adhesive proteins, especially thrombospondin, reside primarily in endogenous pools within the alpha granules of the blood platelets.

Expression of the adhesive proteins on the platelet cell surface is dependent upon platelet stimulation that induces the secretion and release of alpha granule components. This release liberates the adhesive proteins into the extracellular milieu and provides their appearance on the cell surface. Additionally, since adhesive proteins are normally minimally associated with the surface of resting platelets, it is believed that the mechanisms for cell surface expression of adhesive proteins from exogenous sources are also initiated and dependent upon platelet stimulation.

Since platelet activation and localization are fundamental events of injuries to blood vessels, there is a need for methods and reagents capable of detecting and discriminating between activated blood platelets and resting platelets. The ability to detect activated platelets that may react selectively with impaired blood vessel walls would particularly aid in finding the situs of soft tissue injuries, especially in cases of trauma where the victim has no externally apparent injury.

Presently, assays of circulating activated platelets are measured in vitro using the well known platelet aggregate ratio test wherein appropriate dilutions of an unknown antibody-containing sample are incubated with antigen-bearing cells and the antibody concentration (titer) is determined by comparing the resulting agglutination responses to those obtained with a standard antibody-containing sample of known titer. This test, however, is often cumbersome and unreliable.

One current method for imaging blood platelets in vivo involves a time-consuming and inconvenient procedure using $^{111}$indium-labelled platelets. The procedure involves isolating blood platelets from a patient, labelling the platelets with the radionucleotide in vitro and then reinfusing the radiolobelled platelets back into the patient. The $^{111}$indium-labelled platelets can be imaged only after a sufficient period of time passes to reduce background signal interferences.

Thus, a diagnostic site-specific imaging reagent capable of selectively binding and imaging a specific cell membrane-associated adhesive protein would have desirable clinical utility for rapidly indicating the site of stimulated activated platelets and could be useful for discriminating between such platelets and resting platelets.

More partcularly, a diagnostic site-specific imaging reagent comprising an antibody or antibody fragment that binds to a specific blood platelet protein component (when it is expressed as a cell surface antigen of a blood platelet that is in a stimulated activated state) could circumvent many of the technical complexities, inconveniences and time consuming aspects of the presently available in vitro and in vivo diagnostic procedures.

Nieuwenhuis et al. reported a monoclonal antibody against thrombin-activated platelets that does not cross-react with resting platelets [*Thrombosis and Haemostasis*, 50, 100 (1983)]. The monoclonal antibody was prepared against activated platelets using spleen cells from mice immunized with thrombin-activated human blood platelets fused to a murine (mouse) myeloma cell line to form a hybridoma. Anti-platelet antibodies were produced, and one hybridoma produced antibodies that bound to an unknown antigen on thrombin- or ADP-activated platelets. However, the antibody had no functional properties in aggregation studies of platelets stimulated by ADP, epinephrine, collagen, thrombin or the antibiotic, restocetin. The antigen to which the antibody bound was found to be located in a special subclass of blood platelet granules different from alpha granules.

Hsu-Lin et al. also reported the production of monoclonal antibodies specific for thrombin-activated platelets [*Blood*, 62 (Suppl. 1), (1983)] prepared from murine hybridomas using standard methods known in the art. The specificity of the antibodies was to an unidentified single protein component that migrated between glycoprotein IIb and glycoprotein IIIa on separation by Western blotting procedures. The unidentified protein was derived from either solubilized activated platelets or from resting platelets, and had an apparent molecular weight of between about 98,000 and 120,000 daltons.

McEver et al. reported that a monoclonal antibody to platelet membrane glycoprotein IIa binds only to activated platelets [*Blood*, 62 (Suppl 1), (1983)]. The hybridoma was produced from spleen cells of a mouse immunized to thrombin-activated human platelets bound specifically to thrombin-activated platelets but not to peripheral blood mononuclear cells. The specificity of the antibody was to a protein having an apparent molecular weight of about 138,000 (unreduced) and 148,000 (reduced) daltons and fit certain criteria for glycoprotein IIa, which is believed to be a plasma membrane molecule that changes its conformation after platelet activation, or for a granule membrane component that fuses with the plasma membrane during the release reaction. However, the function of the protein is not known.

Thus, a need exists for a pre-labelled antibody to a blood protein component, particularly one located in the subcellular alpha granules capable of indicating the blood component as an expressed cell surface antigen by imaging the site as a means for detecting and localizing the blood component. An indicating site-specific diagnostic reagent could provide a rapid clinical evaluation means in scanning for platelet thrombi.

A particular need exists for a non-invasive rapid clinical method for identifying and localizing the presence of thrombi, especially in heart attack and stroke patients, and for managing in situ thrombolytic therapy in patients having acute myocardial infarction.

A need also exists for detecting in vivo the situs of injured blood vessel walls following an injury or to screen for silent coronary artery disease in individuals at risk.

SUMMARY OF THE INVENTION

The present invention relates to a mammalian diagnostic site-specific imaging reagent, a method of its preparation and use, and to a diagnostic system utilizing that reagent. The reagent comprises a receptor raised in an animal host to a blood platelet cell membrane-associated antigen.

The receptor comprises a monoclonal antibody, a polyclonal antibody or a mixture thereof raised in an animal host to a specific intracellular or extracellular blood protein component that is not normally blood cell membrane-associated. The protein component is a cell membrane-associated antigen that is present at the outer cell surface of a blood platelet when the blood platelet is in a stimulated "active" state and is substantially absent from the outer cell surface of a blood platelet that is in a non-stimulated normal or "resting" intact state as previously described.

The term "antigen" in its various grammatical forms has been used in the art to include materials that are immunogenic. However, more recent usage defines an antigen as that to which a receptor such as a whole antibody binds, and an immunogen as that which induces the production of antibodies in vivo, respectively. An antibody is a protein produced by the immune system of a host animal in response to the presence of a foreign substance, and is also known as an immunoglobulin (Ig). The specificity of an antibody is directed to the immunogen against which it was raised. As used herein, the term "antigen" includes a specific intracellular or extracellular blood protein component used to raise an antibody as well as the protein to which the antibody binds, and the term "receptor" includes an antibody raised in a host animal to that component.

By its very nature, a receptor must be accessible to the exterior cell surface. The phrase "outer cell surface" refers to the exterior cell surface as opposed to the submembranous cytoplasmic surface.

An intracellular component of the antigen comprises a protein that is present in the subcellular platelet granules, in particular the alpha granules, and virtually absent in plasma. An extracellular blood protein component comprises a protein present in normal plasma.

A protein useful as an antigen in this invention is normally absent from the outer cell surface membrane of a resting non-stimulated blood platelet or is present in only minimal amounts. The protein is found expressed as a blood platelet cell membrane-associated antigen in the outer cell surface of activated, stimulated platelets as hereinbefore described.

A preferred protein for use as an antigen in the reagent of this invention comprises a member of the blood protein component group consisting of fibrinogen, fibronectin, von Willebrand factor and thrombospondin. A particularly preferred glycoprotein is a sialoglycoprotein, more particularly thrombospondin.

One aspect of this invention relates to forming a diagnostic site-specific imaging reagent comprising the steps of: immunizing an animal host with a human blood platelet cell membrane-associated antigen in an amount sufficient to induce the production of antibodies to the antigen, the antibodies being receptors for said antigen; maintaining the immunized host for a time period sufficient to form the antibodies to the antigen; withdrawing or collecting antibody-containing antisera from the immunized host; recovering the receptor so produced in substantially pure form; and combining or admixing the recovered receptor with an indicating means.

A particular aspect of this invention relates to a diagnostic site-specific imaging reagent that recognizes a glycoprotein, in particular, a sialoglycoprotein such as thrombospondin when it is expressed as a cell membrane-associated antigen. More particularly, an anti-thrombospondin reagent is contemplated, hereinafter referred to as anti-TSP, that binds to thrombospondin expressed as a cell membrane-associated antigen on the outer cell surface of a stimulated activated blood platelet, and is substantially non-binding to thrombospondin that is not so expressed or that is associated on the outer cell surface of a non-stimulated resting platelet.

Another aspect of the invention relates to a method of forming a monoclonal receptor for use in a site-specific reagent. The method comprises the steps of:

(a) administering to a non-human animal host a human blood platelet cell membrane-associated antigen in an amount sufficient to induce the production of antibodies to the antigen, the antibodies being receptors for the antigen; (b) maintaining the immunized host for a time period sufficient to form the antibodies to the antigen; (c) recovering antibody-producing cells from anti-sera withdrawn from the immunized host; (d) forming hybridomas by fusing the antibody-producing cells with myeloma cells preferably from the host species; (e) culturing the hybridomas so fused in a suitable medium; (f) assaying and selecting the hybridomas for the ability to produce a monoclonal receptor that binds to a cell membrane-associated antigen of a blood platelet when the blood platelet is in a stimulated state, the receptor being substantially non-binding to said platelet when the platelet is not in a stimulated state; and (g) collecting the monoclonal receptor as a product of the hybridomas in a substantially pure form.

The above methods can also include the step of administering to the host after step (a) and a sufficient period of growth, e.g., 1–2 weeks, but before step, (b) a second injection of the same antigen to boost the production of antibody.

The above-described method of forming receptors includes culturing the hybridomas in vitro in a suitable medium and recovering the antibody from the hybridoma supernatant by methods that are well known in the art. This is known as a cell culture system. The above method, in the alternative, can include injecting the hybridoma into an animal host and recovering the antibody from ascites fluid of the host. This is known as a whole animal system. Such whole animal systems tend to produce more antibody per unit volume than cell culture systems, but whole animal systems are sometimes difficult to use if large quantities of antibody are desired.

The present invention includes monoclonal and polyclonal receptors produced by any of the abovedescribed methods. In a still further aspect of the present invention, a method of preparing the above described monoclonal receptor comprises culturing the hybridoma ATCC HB 8680 or 8681 in a suitable medium and recovering the receptor from the supernatant of said hybridoma.

The invention further includes a mammalian diagnostic system such as a kit that includes at least one package containing as an active ingredient a receptor of this invention, that, when combined with an indicating means and introduced into a blood sample, binds selectively to the antigen against which it was raised and is capable of indicating the site of binding. More particularly, the receptor is labelled with an indicating means and binds to a specific blood protein component when the component is expressed as a cell membrane-associated antigen on the outer cell surface of stimulated activated blood platelets to detect and discriminate the activated blood platelet from one that is not so stimulated, and is resting.

The use of a diagnostic site-specific imaging reagent of this invention includes the detection and localization of a cell membrane-associated blood protein component that is normally absent from the outer cell surface of the resting blood platelet and is cell membrane-associated as an antigen on the outer cell surface of an activated blood platelet when a blood sample is assayed in vitro.

An especially preferred use of such a diagnostic reagent relates to the detection of an alpha granule component of blood platelets expressed as a cell membrane-associated antigen of blood platelets in in vitro and in vivo protocols. More particularly, a monoclonal or polyclonal receptor labelled with a physiologically tolerable indicating means provides a non-invasive clinical in vivo method for selectively localizing the situs of activated blood platelets exposed in injured vessel walls.

One benefit of a diagnostic site-specific imaging reagent of this invention is that platelet thrombi can be rapidly scanned to diagnose thromboembolism as occurs in heart attack, stroke, deep venous thrombosis and pulmonary embolism patients to aid in identifying and localizing the site of such thrombi for acute in situ thrombolytic therapy.

Another benefit of the present invention is that the reagent can be used to scan for and image injured vessel walls where thrombospondin has become exposed in the endothelial matrix as a consequence of vessel injury in individuals at risk of silent coronary artery disease.

Still another benefit of this invention is that circulating activated blood platelets can be detected in vitro in blood samples of individuals ingesting prothrombotic medications, such as oral contraceptives.

An advantage of this invention is that it detects activated platelets faster and more reliably than does the well known platelet aggregate ratio test.

A still further advantage is that a reagent of this invention, especially anti-TSP or a conjugate thereof, can be used to localize a blood clot for purposes of improving the therapeutic ratio of an in situ thrombolytic agent, such as tissue plasminogen activator, the natural clot dissolver.

Other advantages and benefits of the present invention will becom readily apparent to those skilled in the art from the following description of the invention and the appended claims.

DETAILED DESCRIPTION OF THE INVENTION

The present invention contemplates a method of detecting and discriminating between stimulated and non-stimulated blood platelets. The invention relates to the formation and use of monoclonal or polyclonal receptors to blood protein components that are released from the alpha granules of resting blood platelets when the platelets are stimulated with an agonist and are expressed as outer cell surface antigens on the activated platelets. The receptor binds to an activated blood platelet having the cell membrane-associated antigen thereon and does not cross-react with normal resting blood platelets as described herein.

The present invention further contemplates a mammalian diagnostic site-specific imaging reagent comprising a receptor as hereinabove described and an indicator labelling means for identifying the site of the cell surface-expressed antigen. A specific blood protein component of the alpha granules is used as a marker and target antigen to illustrate the present invention but the invention is not meant to be so limited.

Thrombospondin is a particularly preferred blood protein component for use as the target antigen as will be discussed in the following sections. Thrombospondin is present in minimal amounts on the outer cell surface of resting platelets but is expressed in detectable quantities on the outer cell surface of activated platelets. It is present in the endogenous intracellular alpha granule pool of blood platelets. In contrast, about 0.1 percent of circulating thrombospondin is free in plasma.

Monoclonal and polyclonal receptors have been raised as described herein that are specific for thrombospondin and that do not cross react with other plasma proteins. Moreover, labelled receptors, as further described herein, bind to thrombin-stimulated blood platelets and are substantially non-binding to non-stimulated platelets. Thus, a receptor of this invention can provide an imaging reagent of this invention that detects and discriminates activated blood platelets from resting blood platelets in a site-specific manner.

I. Introduction

Blood protein components that are expressed on the outer cell surface of activated platelets as adhesive proteins can be derived from the endogenous intracellular alpha granule pool or from exogenous sources, such as plasma or the subendothelial matrix. A comparison of approximate amounts of the adhesive proteins present in these potential sources is shown in Table I.

TABLE I

| Adhesive Protein | Platelet Content (micrograms/$10^9$ platelets) | Plasma Content (microqrams/ml) |
| --- | --- | --- |
| Fibrinogen | 50 | 3,000 |
| Fibronectin | 3 | 300 |
| von Willebrand Factor | 2 | 20 |
| Thrombospondin | 20 | 0.02 |

Thus, plasma is an inconsequential source of thrombospondin and a substantial source of fibrinogen, fibronectin and von Willebrand Factor. Assuming infinite affinity, complete binding of thrombospondin to blood platelets would only place about 50 to 300 molecules of the blood protein component per cell.

On the other hand, thrombospondin is a major blood platelet component of the alpha granule pool that is known to be cell surface expressed following thrombin-stimulation of the cell. Surface expression of thrombospondin occurs in the presence of divalent metal ions, such as calcium and magnesium, but is reduced by ethylenediaminetetraacetic acid (EDTA). Serum levels of thrombospondin are about 10,000–30,000 nanograms/milliliter (ng/ml), which suggests a platelet content of approximately 20,000 ng/$10^9$ cells.

The endothelial matrix cells provide an exogenous source of fibronectin, von Willebrand Factor and thrombospondin. Thrombospondin is synthesized by endothelial cells, smooth muscle cells, monocytes, and fibroblasts and is incorporated into the subcellular matrix. Intrinsic labelling studies show that thrombospondin is synthesized at a rate of about 10 to 71 ng/$10^4$ cells over a period of 18 hours as reported by Raugi et al., "Thrombospondin: Synthesis and Detection by Cells in Culture", *J. Cell. Biol.*, 95, 351 (1982). Other studies are found in Mosher et al., "Synthesis and Secretion of Thrombospondin by Cultured Endothelial Cells", *J. Cell. Biol.*, 93, 343 (1982) [hereinafter Mosher et al.], and in Jaffe et al., "Cultured Human Fibroblasts Synthesize add Secrete Thrombospondin and Incorporate it into Extracellular Matrix", *Proc. Natl. Acad. Sci. (U.S.A.)*, 80, 998 (1983) [hereinafter Jaffe et al. (1983)].

The role of thrombospondin in platelet aggregation is not fully understood but it is known to be the molecule on the stimulated platelet surface that is responsible for agglutinin activity. This finding was reported by Jaffe et al., "Thrombospondin is the Endogenous Lectin of Human Platelets", *Nature*, 295, 246 (1982) [hereinafter Jaffe et al. (1982)].

It is believed that thrombospondin plays a role in platelet aggregation via an interaction with fibrinogen, since fibrinogen can support platelet aggregation in the absence of platelet secretion where thrombospondin is unavailable or is only available in diminished amounts in the platelet (e.g., Gray platelets). In contrast, however, Nurden et al., have reported the "Inhibition of Thrombin-induced Platelet Aggregation of a Rabbit Antibody Against Human Platelet Thrombospondin", in *Thrombosis and Haemostosis*, 50, (Abst.) 401 (1983).

The function of thrombospondin synthesized by fibroblasts is also unclear. Using mouse monoclonal anti-thrombospondin and rabbit polyclonal anti-thrombospondin, Jaffe et al. (1983) localized thrombospondin to the fibrillar extracellular matrix of cultured human fibroblasts by means of immunofluoresence microscopy. It was reported that human foreskin and fetal lung fibroblasts, respectively, secreted thrombospondin in a time-dependent manner at the rate of about 15.7 and 5.8 micrograms per $10^6$ cells per 24 hour period into the culture medium as determined by enzyme-linked immunoabsorbent assay (hereinafter ELISA).

II. GENERAL DISCUSSION

The term "receptor" as used herein is meant to indicate a biologically active molecule that binds to an antigen. A receptor molecule of the present invention is an intact antibody, substantially intact antibody or an idiotype-containing polypeptide portion of an antibody in subtantially pure form, such as in ascites fluid or serum of an immunized animal.

Biological activity of a receptor molecule is evidenced by the binding of the receptor to its antigenic ligand upon their admixture in an aqueous medium, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polypeptide portions (antibody combining sites) of antibodies are those portions of antibody molecules that include the idiotype and bind to the ligand, and include the Fab, Fab' and F(ab')$_2$ portions of the antibodies. Fab and F(ab')$_2$ portions of antibodies are well known in the art, and are prepared by the reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and then alkylation of the resulting protein mercaptan with reagent such as iodoacetamide. Intact antibodies are preferred, and will be utilized as illustrative of the receptor molecules of this invention.

The receptors useful in the present invention are monoclonal or polyclonal receptors. A "monoclonal receptor" (Mab) is a receptor produced by clones of a single cell called a hybridoma that secretes but one kind of receptor molecule. A "polyclonal" receptor (Pab) is a receptor produced by clones derived from different cells that secrete different antibodies that bind to a plurality of epitopes of the immunogenic molecule. The preparation of polyclonal receptors is discussed hereinafter as part of the production of Mabs.

The hybridoma cell is fused from an antibody-producing cell and a myeloma or other self-perpetuating cell line. Such receptors were first described by Kohler and Milstein, *Nature*, 256, 495 (1975), which description is incorporated herein by reference. Monoclonal receptors are typically obtained from hybridoma tissue cultures, the preferred method for obtaining a monoclonal receptor of the present invention, or, alternatively, from ascites fluid obtained from non-human, warm blooded host animals into which the hybridoma tissue was introduced.

Attibodies are secreted by specialized cells called B cells (bone marrow-derived lymphocytes). Each B cell secretes one type of antibody having a single specificity so the various antibodies of different specificites are each secreted by different B cells. The B cells are cloned to provide a source of the antibodies. However, B cells die in a few days in culture media and must be made relatively "immortal" so that a supply of the desired antibodies may be obtained. This is accomplished by removing the B cells from the animal, typically from the spleen, fusing the B cells with a cancerous or myeloma cell to form a cell hybrid (called "a hybridoma") and then culturing the hybridoma. Both methods are described hereinafter.

To form a hybridoma from wich a monoclonal receptor is produced, a myeloma cell line is fused with an antibody-producing cell that produces antibodies that react with a blood protein component, such as splenocytes from a mammal immunized with thrombospondin as an immunogen.

The antibody-producing cells that are employed may be derived from any mammal, such as primates, humans, rodents (e.g., mice and rats), rabbits, cattle, dogs, sheep or the like. As appropriate, a non-human host animal may be immunized by injection of an immunogen, in this instance thrombospondin, followed by a booster injection, and then isolation of the spleen after a sufficient time period has elapsed for the host to produce antibodies, this is typically about one month to about three months after the first immunization.

Non-human, warm blooded animals usable in the present inventions as hosts can include poultry (such as a chicken or a pigeon), a member of the ratitae bird group (such as an emu, ostrich, cassowary or moa) or a mammal (such as a dog, cat, monkey, goat, pig, cow, horse, rabbit, guinea pig, rat, hamster or mouse). Preferably the host animal is a mouse, rabbit or emu.

It is prefereed that a myeloma cell line be from the same species as the antibody-producing cells. Therefore, fused hybrids such as mouse-mouse hybrids [Shulman et al., *Nature*, 276, 269 (1978) or rat-rat hybrids (Galfre et al., *Nature*, 277, 131 (1979)] are typically utilized. However, some rat-mouse hybrids have also been successfully used in forming hybridomas [Goding, "Production of Monoclonal Antibodies by Cell Fusion", in *Antibody as a Tool*, Marchalonis et al. eds., John Wiley & Sons Ltd., 273–289 (1982) hereinafter Marchalonis et al.]. Suitable myeloma lines for use in the present invention include MPC-11 (ATCC CRL 167), P3X63-Ag8.653 (ATCC CRL 1580), Sp 2/0-Ag14 (ATCC CRL 1581), P3X63Ag8U.1 (ATCC CRL 1597), Y3-Ag1.2.3 (deposited at Collection Nationale de Cultures de Microorganisms, Paris, France, number I-078 and P3X63Ag8 (ATCC TIB9). Myeloma line X63.657 is preferred for use in the present invention.

Monoclonal anti-thrombospondin (anti-TSP) receptors were formed as described herein from murine (mouse) myeloma lines, and polyclonal antithrombospondin receptors were formed from rabbit and from emu myeloma lines. The monoclonal anti-TSP reagents were given the following designations for reference purposes and were deposited with the American Type Culture Collection (ATCC), 12301 Parklawn Drive, Rockville, Md. 20852 U.S.A. on December 12, 1984 under the following ATCC accession numbers.

| Monoclonals | ATCC Accession Number |
|---|---|
| TSP I-1 (14E7) | HB 8680 |
| TSP I-2 (9D7) | HB 8681 |

Receptors are utilized along with an indicator labeling means or "indicating group" or a "label". The indicating group or label is utilized in conjunction with the receptor as a means for determining the site of a specific cell surface expressed antigen, and in some instances for determining the extent of a reaction between the receptor and the antigen.

The terms "indicator labeling means", "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry and constitute a part of this invention only insofar as they are utilized with otherwise novel receptors, methods and/or systems.

The indicator labelling means can be a fluorescent labelling agent that chemically binds to antibodies or antigens without denaturing them to form a fluorochrome (dye) that is a useful immunofluorescent tracer. Suitable fluorescent labelling agents are fluorochromes such as fluorescein isocyanate (FIC), flourescein isothiocyanate (FITC), dimethylamino-naphthalene-S-sulphonyl chloride (DANSC), tetramethylrhodamine isothiocyanate (TRITC), lissamine, rhodamine B200 sulphonyl chloride (RB 200 SC) and the like. A description of immunofluorescence analysis techniques is found in Marchalonis et al., "Immunofluorescence Analysis", 189–231, which is incorporated herein by reference.

The indicating group may also be an enzyme, such as horseradish peroxidase (HRP) or glucose oxidase, or the like. Where the principal indicating group is an enzyme such as HRP or glucose oxidase, additional reagents are required to visualize the fact that a receptor-ligand complex has formed. Such additional reagents for HRP include hydrogen peroxide and an oxidation dye precursor such as diaminobenzidine. An additional reagent useful with glucose oxidase is 2,2'-azino-di-(3-ethylbenzthiazoline-6-sulfonic acid) (ABTS).

A particularly preferred fluorescent labelling agent is fluorescein isothiocyanate. Cell-bound fluorochrome is determined by fluorescence microscopy using an activated cell sorter (FACS) such as that sold by Ortho Diagnostics of Westwood, Mass. The expression of blood protein antigen on the outer cell surface of activated blood platelets increases fluorescein fluorescence intensity due to binding of a labelled receptor of this invention as described hereinbelow.

An exemplary radiolabelling agent is a radioactive element that produces gamma ray emissions. Elements which themselves emit gamma rays, such as $^{124}I$, $^{125}I$, $^{128}I$, $^{131}I$, $^{132}I$, and $^{51}Cr$ represent one class of gamma ray emission-producing radioactive element indicating groups. Particularly preferred is $^{125}I$. Another class of useful indicating groups are those elements such $^{11}C$, $^{18}F$, $^{15}O$ and $^{13}N$ which themselves emit positrons. The positrons so emitted produce gamma rays upon encounters with electrons present in the animal's body. Also useful is a beta ray emitter, such as $^{111}$indium.

A preferred radioactively labelled monoclonal receptor can be prepared by culturing hybridoma cells in a medium containing radioactive amino acids, as is well known, as well as by isolating the monoclonal receptor and then labelling the monoclonal receptor with one of the above radioactive elements as described in U.S. Pat. No. 4,381,292 to Bieber and Howard, incorporated herein by reference.

A radiolabelled receptor such as anti-TSP or an idiotype-containing polypeptide portion thereof is then introduced as by injection into the blood stream of a mammal having a vascular disease, especially an arterial thrombosis, or vessel wall injury. The labelled receptor forms a complex with the thrombospondin on the outer cell surface thrombin-stimulated activated blood platelets whose situs may be determined after a suitable, predetermined time (about 18 to about 24 hours) to permit clearance of unbound labelled receptor from the body.

The mammal is scanned with a gamma ray emission detector such as the axial tomographic scanner commercially available under the designation CT (8--800 CT/T) from General Electric Company (Milwaukee, Wis.), or with a positron emission transaxial tomography scanner such as that designated Pett VI located at Brookhaven National Laboratory. Such scanning provides an image of the activated blood platelet, as well as information as to the sites and size of a blood clot or injured soft tissue because of the specificity of the radiolabelled receptor utilized.

In another embodiment, a receptor can be labelled with an indicating group containing an element that is active in nuclear magnetic resonance (NMR) spectroscopy; i.e. an NMR-active element. Many such elements are commercially available in addition to the more usual $^{13}C$, $^{15}N$, $^{19}F$ and the like.

It is particularly preferred to utilize an indicating group containing the NMR-active $^{19}F$ atom, or a plurality of such atoms inasmuch as (i) substantially all of naturally abundant fluorine atoms are the $^{19}F$ isotope and thus substantially all fluorine-containing compounds are NMR-active; (ii) many chemically active polyfluorinated compounds such as trifluoroacetic anhydride are commercially available at relatively low cost, and (iii) many fluorinated compounds have been found medically acceptable for use in humans such as the perfluorinated polyethers utilized to carry oxygen as hemoglobin replacements.

Another particular advantage of the use of fluorine-containing NMR-active indicating groups is that a mammalian body contains very little fluorine under normal conditions. Consequently, by using an NMR-active element that is otherwise substantially absent from the mammal, background signals owing to bodily fluorine atoms are substantially absent. Thus, the principal signals observed are due to a labelled receptor—blood protein component complex.

In one embodiment, a receptor such as anti-TSP is preferably labelled with a fluorine-containing material such as trifluoroacetic anhydride or hexafluoroethanol to form a fluorinated amide or ester derivative, respectively. Thereafter, the fluorinated receptor is introduced as by injection into the bloodstream of a mammal subjected to a vascular injury. After a predetermined amount of incubation time for the labelled receptor to complex with expressed thrombospondin on the activated blood platelet surface and for any uncomplexed receptor to be cleared from the body, a so-called "whole-body" NMR determination is carried out using an apparatus such as one of those described by Pykett, *Scientific American*, 246, 78 (1982) to locate and form an image of the activated blood platelet.

Indicating means or labels that are themselves radioactive such as the before-mentioned gamma ray, beta ray and positron emitters, and the NMR-active elements are preferably utilized within the body of the mammal to be assayed and may thus be referred to as in vivo labels or indicating means. The more general terms "indicating means", "indicating group" and "label" are utilized herein where an in vivo label or a label that is less useful within the body of the assayed mammal such as a fluorochrome dye or enzyme is intended.

The indicating means may be bonded to the receptor as where an antibody is labelled with $^{125}I$. The means may also constitute all indicator or a portion of a separate molecule or atom that reacts with the receptor molecule such as HRP-linked to rabbit anti-mouse antibodies where the antibody receptor was raised in a mouse, or where a radioactive element such as $^{125}I$ is bonded to protein A obtained from *Staphylococcus aureus*.

An indicator labelling agent is preferably supplied along with the receptor and may be packaged therewith or packaged separately. Additional reagents such as hydrogen peroxide and diaminobenzidine may also be included in the system when an indicating group such as HRP is utilized. Such materials are readily available in commerce, as are many indicating groups, and need not be supplied along with the diagnostic system. In addition, some reagents such as hydrogen peroxide may decompose on standing, or are otherwise short-lived like some radioactive elements, and are better supplied by the end-user.

Thus, the above methods of detecting the site of activated blood platelets in vivo in a mammal include the following steps.

(a) Providing a composition containing an effective amount of a receptor of the present invention wherein the receptor such as anti-TSP is bonded to an in vivo indicating group. Typical compositions include about 1 to about 100 milligrams of the labelled receptor in an aqueous, physiologically tolerable medium such as that provided by water alone, an aqueous saline, phosphate-buffered saline (PBS) or other aqueous buffer solution. The amount of receptor utilized depends, inter alia, upon the mammal, the vascular stimulating event and the class of receptor, where an intact antibody is used. The useful indicating groups include gamma ray emission-producing elements, NMR-active elements and the like, as noted before.

(b) The composition so provided is introduced as by injection into the bloodstream of a mammal to be assayed for the presence of activated blood platelets as are produced by a thrombotic vascular stimulating event.

(c) The mammal so injected is maintained for a predetermined period of time sufficient for the indicating group-bonded (labelled) receptor to form a complex on the surface of the activated blood platelet, and for any uncomplexed labelled receptor to clear from the body.

(d) The mammal is then scanned with a means for detecting the location of the complexed, labelled receptor. Typical detecting means include usually used gamma ray emission detectors, those machines used in positron emission tomography and so-called "whole body" NMR spectrometers which may in practice only scan a portion of the body at any time.

The present invention further contemplates a method of preparing a receptor of this invention, a method of assaying using such a receptor and a diagnostic system that includes a receptor of this invention in packaged form. The following discussion describes several specific, illustrative embodiments of the present invention with emphasis on particularly preferred receptors, their preparation and use as exemplary of the more general invention.

III. Specific Embodiments

A. Formation of Monoclonal Anti-TSP

Human platelet thrombospondin was released from 1 to 3 day old platelet concentrate obtained from platelet concentrate by activating the platelets with thrombin, isolating the thrombospondin and purifying it as described by Lawler et al., *J. Biol. Chem.*, 23, 8609 (1978). Briefly, stable, soluble thrombospondin was isolated in physiological saline by a combination of exclusion and affinity chromatography. The purity of the thrombospondin (TSP) preparation was greater than 95 percent as determined by isoelectric focusing and sodium dodecyl sulfate-polyacrylamide gel electrophoresis (SDS-PAGE) analysis.

Monoclonal anti-TSP was formed using the standard hybridoma technology of Kohler et al., *Nature*, 256, 495 (1975). Briefly, BALB/c mice were immunized by intraperitoneal injection with approximately 25 micrograms per mouse of the thrombospondin preparation emulsified in complete Freund's adjuvant. The mice were reimmunized with 25 micrograms of the thrombospondin preparation in an equal volume of incomplete Freund's adjuvant at days 14, 26, 36 and 47.

Subsequently, each mouse was bled from the retroorbital plexus. Sera obtained were screened for anti-thrombospondin antibodies using a solid phase radioimmunoassay with $I^{125}$-goat-anti-mouse immunoglobulin (Sigma Chem. Co., St. Louis, Mo.) as the antibody identifying agent and 2.5 micrograms per milliliter thrombospondin coated on each well as the solid phase antigen.

The two mice with the highest titers of anti-TSP antibodies were selected for further immunization, and were reimmunized on day 90 after the initial immunization with 20 micrograms of the TSP preparation intravenously and 20 micrograms of the TSP preparation intra-peritoneally. The mice were immunized again on day 93 with 40 micrograms of the thrombospondin preparation and the mouse with the highest titer of anti-TSP antibodies was selected for the cell fusion.

The mouse was sacrificed three days after the last immunization. The spleen of that mouse was removed, and the splenocytes were isolated and suspended in an appropriate medium. This experimental technique is well known in the art. A suitable medium is HAT (hypoxanthine, aminopterin and thymidine) and about 1 milliliter (ml) of medium per spleen is sufficient. Another suitable medium is Dulbecco's Modified Eagle's Medium containing 10 percent of fetal calf serum (CFS).

The splenocytes were pooled to yield $1.5 \times 10^8$ total cells. The cells were subsequently fused with unfused murine (mouse) myeloma cell line X63.657 in the presence of a suitable cell fusion promoter to provide a composition that contains unfused splenocytes, unfused myeloma cells, and fused, hybridoma cells. A suitable fusion promoter is a polyethylene glycol (PEG) having a molecular weight of from about 1000 to about 4000 (commercially vvailable as PEG 1000 and PEG 4000 from Sigma Chemical Co., St. Louis, Mo.).

A total volume of about 0.5-1.0 milliliters (ml) of fusion medium is typically appropriate for $10^8$ splenocytes fused with about $3 \times 10^7$ myeloma cells. A preferred ratio is about one myeloma cell per ten spleen cells as described by Curtiss et al., *J. Biol. Chem.*, 257, 15213 (1982).

Many mouse myeloma cell lines are known and are avaiaable from various deposit banks, such as the Salk Institute Cell Distribution Center, La Jolla, Calif. According to accepted practices, the mouse myeloma cell line should preferably be of the "drug resistant" type, so that unfused myeloma cells will not survive in a selective medium, while hybrids will survive. The most common class is 8-azaguanine resistant cell lines, which lack the enzyme hypoxanthine guanine phosphoribosyl transferase and thus will not be supported by HAT medium.

The mixture of unfused spleen cells, unfused myeloma cells and fused cells was diluted and cultured in separate containers in the selective, HAT, medium for a sufficient period of time (about ten to fourteen days) to allow the unfused cells to die. The word "container" refers herein particularly to a well of a microtiter plate or tissue culture plate, although other suitable containers may also be utilized.

Specifically, three days after fusion, viable cells were plated out in 96-well tissue culture plates at $2 \times 10^4$ viable cells per well (about 3,500 total wells) in HAT medium. The plated cells were fed seven days after fusion with HAT medium and at approximately 4-5 day intervals thereafter as needed. Growth was followed microscopically and culture supernatants that contained antibodies were collected on day 14 after fusion for assay of antigen-specific antibody production by solid phase radioimmunoassay (RIA). On day 14, 700 of the 3,500 wells contained colonies of viable cells.

Twenty-five wells or less than one percent of the culture supernatants reacted with human thrombospondin (contained anti-TSP) as measured by solid phase immunoassay using goat anti-mouse immunoglobulin. Six of those twenty-five wells (designated 9D3, 11F3, 14E7, 9D7, 11D7 and 13F5) were selected 22 days after fusion for differential screening; i.e. no reaction with normal human resting blood platelets, but good reaction with human activated blood platelets, and were recloned by limiting dilution in which the volume of diluent was statistically calculated to isolate a certain number of cells (e.g., 1-4) in each separate container (e.g., each well of a microtiter plate).

After a suitable period for hybridoma growth and antibody secretion was elapsed (14-28 days), the resulting supernatants in each container were evaluated for the isotype of the secreted anti-TSP with a Litton Bionetics Kit (Litton Bionetics, Kensington, Md.) as described in the kit instructions. The desired hybridoma was selected and anti-TSP was recovered from the culture supernatant.

Cloned hybridomas were cultivated in a medium containing 10 percent fetal calf serum (FCS) and were stored frozen in liquid nitrogen as described by Kennedy et al., *Diabetes*, 31 (Suppl. 3), 52 (1982).

Once the desired hybridoma is selected and cloned, the resultant antibody may be produced in one of two ways. The more pure monoclonal antibody is produced by in vitro culturing of the desired hybridoma in a suitable medium for a suitable length of time, followed by recovery of the desired antibody from the supernatant. The suitable medium and length of culturing time are known or are readily determined. The in vitro technique produces receptors essentially free from other specific immunoglobulin that immunoreacts with a human-derived antigen (anti-human immune globulin). There is a small amount of other immune globulin present since the medium contains exogenous serum (e.g., fetal calf serum). However, this in vitro method may not produce a sufficient quantity or concentration of antibody for some purposes.

To produce a much greater concentration of slightly less pure monoclonal antibody, the desired hybridoma can be injected into pristane (Aldrich Chem. Co., Milwaukee, Wis.) primed mice, preferably syngenic or semi-syngenic mice to the mouse from which the splenocytes were obtained. The hybridoma causes formation of antibody-producing tumors after a suitable incubation time, which result in a relatively high concentration of the desired antibody in the bloodstream and peritoneal exudate (ascites) of the host mouse. Although these host mice also have normal antibodies in their blood and ascites, the concentration of these normal antibodies is only about 5 percent of the monoclonal antibody concentration. Moreover, since these normal antibodies are predominantly not anti-human in their specificity, the monoclonal antibodies obtained from the harvested ascites or from the serum are essentially free of any contaminant anti-human immune globulin.

Immunoglobulin heavy and light chains of the antibodies secreted by the cloned hybridomas were typed using the Mono AB-ID EIA Kit A (lot Number 20920, Zymed Labs Inc., San Francisco, Calif.). The assays were performed with hybridoma culture supernatants as described by the manufacturer.

Ascites were prepared from five of the above six cell lines (9D3, 11F3, 14E7, 9D7 and 11D7). In the case of all antibodies except those of 9D3, a single band was observed in cellulose acetate electrophoresis which further confirms monoclonality.

In the case of 9D3, three bands were observed. For this reason this cell line was subcloned and ascites were raised from two of the original clones and two of the subclones. In each case, this three band pattern was observed and suggests that this line is also monoclonal. The three bands are probably due to a recombination of the heavy and light chains of the antibody with myeloma proteins produced by the parent myeloma line.

Cell line 14E7 (ATCC HB 8680) was typed as producing an $IgG_{2a}$ antibody (Mab TSP I-1) with a kappa light chain by Ouchterlony immunodiffusion. Mab TSP I-1 has a titer in solid phase radioimmunoassay (as described herein at Section III C) against human thrombospondin of $10^8$, and it does not react with human fibrinogen or fibronectin. In addition, Mab TSP I-1 exhibits a single major band of gamma mobility on cellulose acetate electrophoresis. On Western blots of purified thrombospondin, or human platelets, the antibody reacts with a single polypeptide of apparent subunit molecular weight of 80,000 daltons, which is consistent with the known subunit molecular weight of thrombospondin. On immunofluorescent staining (see Section III D(1) herein), the antibody stains platelet alpha granules, which are known to be the storage site of thrombospondin.

Cell line 9D7 (ATCC HB 8681) produces a monoclonal antibody designated "Mab TSP I-2" which exhibits properties similar to those of Mab TSP I-1, but recognize a distinct epitope.

B. Formation of Polyclonal Anti-TSP

As previously described with reference to the formation of monoclonal anti-TSP, polyclonal anti-TSP was produced using a thrombospondin preparation purified according to Lawler et al., *J. Biol. Chem.*, 23, 8609 (1978).

Rabbits were immunized with 1 milligram (mg) subcutaneous doses of thrombospondin in complete Freund's adjuvant on a bimonthly basis.

Subsequently, each rabbit was bled and sera were screened for anti-thrombospondin antibodies using a solid phase radioimmunoassay with $I^{125}$-goat-antimouse immunoglobulin (Sigma Chemical Co., St. Louis, Mo.) and 2.5 micrograms per milliliter thrombospondin coated on each well, as described before.

C. Solid Phase Radioimmunoassay (RIA)

Assays were performed in flexible round bottom polyvinyl chloride microtiter plates (Falcon, Micro Test III, Becton Dickinson and Co., Oxnard, Calif.). The wells were coated with thrombospondin antigen by adding 0.05 milliliters of thrombospondin in PBS and incubating the plates for 3 hours at room temperature to give a constant final solid phase-bound antigen concentration. All antigens were coated at 1 microgram per milliliter. The wells were "post-coated" for 30 minutes with 0.25 milliliters of PBS containing 3 percent bovine serum albumin (BSA) and 3 percent normal goat serum to block the remaining active sites.

For assays, aqueous media containing 0.05 milliliters of mouse serum or hybridoma culture supernatant were diluted to 0.25 ml in with a solution of PBS containing 3 percent BSA, 3 percent goat serum and 0.05 percent polyoxyethylene (20) sorbitan monolaurate (TWEEN-20) were added to each well to contact the solid phase-bound antigen, and form a solid/liquid phase admixture. The solid/liquid phase admixture was maintained (incubated) for a time period sufficient for anti-TSP antibodies present in the serum or supernatant to immunoreact with the antigen for (18 hours at 4 degrees C.). The solid and liquid phases were separated, and the solid phase was washed.

After washing, immunoreacted mouse antibody; i.e. antibody that bound to the solid phase antigen, was detected by admixture of a composition containing 10 ng per well of immunochemically purified, radioiodinated goat anti-murine immunoglobulin (3 to 4 microcuries per microgram) to form a second solid/liquid phase admixture. The second solid/liquid phase admixture was maintained for a time period sufficient for the goat anti-murine antibodies to immunoreact with and bind to any solid phase-bound antibodies present, e.g., for 4 hours, at 4 degrees C. as is described in Curtiss et al., supra.

The second solid/liquid phase admixure was separated, and the separated solid phase was typically washed to remove any adherent, non-specifically bound radioiodinated goat anti-murine antibodies. The amount of goat bound anti-murine antibodies bound to the solid phase was then determined and the titers were obtained using standard, well known techniques.

Competitive assays were performed in a similar manner and contained 0.025 milliliters of competitor diluted in PBS containing 3 percent bovine serum albumin, 3 percent goat serum and 0.05 percent TWEEN-20, and 0.025 milliliters of culture supernatants containing limiting amounts of monoclonal antibody. Non-specific binding was determined by replacing specific hybridoma culture supernatants with similar dilutions of the culture supernatants of non-related hybridomas producing immunoglobulins of the same heavy chain type.

The maximum amount of $^{125}$I-second antibody bound by specific antibody ($B_o$) was determined in the absence of competitors. Data were calculated as $B/B_o$ where B represents the mean counts per minute of antibody bound at a given concentration of competitor. A control monoclonal antibody was anti-apolipoprotein B.

D. Preparation of Imaging Reagent

(1) Fluorescence Procedure

Immunofluorescent staining was performed on 2 percent formaldehyde fixed platelets on polylysinecoated, circular glass cover slips. The cells were treated for about 3 minutes with 0.1 percent Triton X-100 to render them permeable to antibody and incubated for about 20 minutes with anti-TSP antibody. The cells were rinsed with PBS and stained for about 20 minutes with rhodamine-labelled rabbit F(ab')$_2$ anti goat immunoglobulin (Cappel Laboratories, Cochranville, Pa.). The platelets were viewed with a Zeiss universal microscope equipped with an HBO 50 W mercury lamp and an IVFI epifluorescence condenser (Carl Zeiss, Inc., New York).

(2) Radiolabelling Procedrre

Anti-TSP antibody was radiolabelled with $^{125}I$ to a specific activity of about 0.5 microcuries per microgram, and a double antibody radioimmunoassay was performed substantially as described in Plow et al., *J. Immunol.*, 107, 1495 (1971) which is incorporated herein by reference.

Assays were performed in plastic, siliconized tubes at about 22° C. with $^{125}I$-labelled antibody at a final concentration of about 15 ng/ml in a buffer system of 0.025 molar NaCl, 0.04 molar sodium borate, 1 millimolar EDTA at about pH 8.3.

E. Diagnostic Systems

A diagnostic system, preferably in kit form, comprises yet another embodiment of this invention. This system is useful for detecting and discriminating between activated and resting blood platelets in a blood of cell surface expressed blood protein component. This system includes at least one package that contains an effective amount of biologically active receptor of this invention. That is, a receptor that binds to an activated blood platelet but not to a resting blood platelet.

A predetermined amount of the receptor is admixed with a predetermined amount of platelet-containing blood sample in the presence of an appropriate indicating means. The admixture is maintained for a time period sufficient for the receptor to immunoreact with activated platelets that may be present in the sample, i.e. the admixure is maintained for a time sufficient for a complex to form between the receptor and the cell surface-expressed protein against which the receptor was raised. The indicating means is utilized to signal the formation of the complex after the platelets have been separated from the remaining sample.

An aqueous solution of the receptor in hybridoma supernatant, ascites fluid or buffer may be admixed with the indicator labelling means to admix as a liquid reagent with the blood sample. Alternatively, the reagent may be coated on the walls of a microtiter plate and then admixed with a thrombin-stimulated blood sample; or the thrombin-stimulated blood sample may be coated on microtiter plate walls or on a nitrocellulose sheet or may be present in a tissue section hybridoma supernatant, ascites fluid or a buffer solution containing the reagent admixed herewith.

The results discussed herein were obtained with monoclonal antibodies produced by hybridomas ATCC HB 8680 and HB 8681 of this invention. It is to be understood, however, that the results discussed herein are illustrative of embodiments utilizing the above monoclonal antibodies and the present invention is not intended to be so limited.

What is claimed is:

1. A hybridoma having the ATCC accession number HB 8680 that produces a receptor that immunoreacts with thrombospondin.

2. A hybridoma having the ATCC accession number HB 8681 that produces a receptor that immunoreacts with thromobospondin.

3. A monoclonal hybrdoma culture comprising the hybridoma ATCC HB 8680 in a nutrient medium.

4. A monoclonal hybridoma culture comprising the hybridoma ATCC HB 8681 in a nutrient medium.

5. A receptor that immunoresacts with thrombospondin produced by the hybridoma ATCC HB 8680.

6. A receptor that immunoreacts with thrombospondin produced by the hybridoma ATCC HB 8681.

7. A diagnostic site-specific imaging reagent comprising a receptor produced by a hybridoma selected from the group consisting of hybridomas ATCC HB 8680 and ATCC HB 8681, and indicating means labeling said receptor, wherein said receptor is capable of selectively binding to a blood platelet in a stimulated state, but is substantially non-binding to non-stimulated platelet.

8. The reagent of claim 7 wherein the indicating means is a fluorescent labelling agent.

9. The reagent of claim 7 wherein the indicating means is a radiolabelling agent.

10. The reagent of claim 7 wherein the indicating means is $^{111}$-indium.

11. The reagent of claim 7 wherein the indicating means is $^{125}$-Iodine.

12. A method for detecting and discriminating between stimulated blood platelets and non-stimulated blood platelets comprising the steps of:
    (a) admixing a blood platelet-containing sample with the diagnostic site-specific imaging reagent of claim 1;
    (b) maintaining said admixture for a time period sufficient for said reagent to immunoreact with any stimulated platelets present and form a complex; and
    (c) determining the presence of a complex and thereby stimulated platelets by a signal from the indicating means of said reagent.

13. The method of claim 12 wherein the imaging is performed in vitro.

14. The method of claim 12 wherein the imagining is performed in vivo.

15. The method of claim 12 wherein said stimulated blood platelet is thrombin-stimulated.

16. A diagnostic system for detecting a thrombus in vivo in a mammal in kit form containing in at least one package an effective amount of anti-thrombospondin receptors labeled with an in vivo indicating means said receptors capable of binding to a blood platelet in a stimulated state, but not substantially binding to a non-stimulated blood platelet.

17. The diagnostic system of claim 16 wherein said anti-thrombospondin receptors are those produced by hybridoma ATCC HB 8680.

18. The diagnostic system of claim 16 wherein said anti-thrombospondin receptors are those produced by hybridoma ATCC HB 8681.

19. The diagnostic system of claim 16 wherein said anti-thrombospondin receptors are in an aqueous buffer.

20. The diagnostic system of claim 16 wherein said indicating means contains an NMR-active element that is otherwise substantially absent from the mammal diagnosed for a thrombus.

21. The diagnostic system of claim 20 wherein said indicating means is chosen from the group consisting of $^{13}C$, $^{15}N$, and $^{19}F$.

22. The diagnostic system of claim 16 wherein said indicating means is $^{111}$indium.

23. A method for detecting the presence of a thrombus in a mammal comprising the steps of:
 (a) intravenously injecting into the mammal an effective amount of anti-thrombospondin receptors that are labeled with an in vivo indicting means, said anti-thrombospondin receptors binding to a blood platelet in a stimulated state, but not substantially binding to a non-stimulated blood platelet;
 (b) maintaining the injected mammal for a predetermined period of time sufficient for the receptors to react with thrombospondin present in the mammal on the surface of platelets in a thrombus and form a complex; and
 (c) assaying for the presence of any complex that formed in step (b).

24. The method of claim 23 wherein the anti-thrombospondin receptors are those produced by hybridoma ATCC HB 8680.

25. The method of claim 23 wherein the anti-thrombospondin receptors are those produced by hybridoma ATCC HB 8681.

26. The method of claim 23 wherein said injected and maintained mammal of step (b) is further prepared for assaying according to step (c) by maintaining said mammal for a predetermined time period sufficient for any uncomplexed labeled receptor to clear from the body of said mammal.

* * * * *

UNITED STATES PATENT AND TRADEMARK OFFICE
CERTIFICATE OF CORRECTION

PATENT NO. : 4,820,505

DATED : April 11, 1989

INVENTOR(S) : Mark H. Ginsberg and Edward F. Plow

It is certified that error appears in the above-identified patent and that said Letters Patent is hereby corrected as shown below:

Column 1, line 4, after the title and before the heading "TECHNICAL FIELD", insert the following paragraph:

--This invention was made with government support under Contract Nos. HL 16411 and HL 28235 awarded by the National Institutes of Health. The government has certain rights in the invention.--

Signed and Sealed this

Fourth Day of January, 1994

*Attest:*

BRUCE LEHMAN

*Attesting Officer*    *Commissioner of Patents and Trademarks*